(12) United States Patent
Kurzenberger

(10) Patent No.: US 10,366,255 B2
(45) Date of Patent: Jul. 30, 2019

(54) BARCODE SCANNING DEVICE FOR DETERMINING A PHYSIOLOGICAL QUANTITY OF A PATIENT

(75) Inventor: Heinz Otto Kurzenberger, Deckenpfronn (DE)

(73) Assignee: KONINKLIJKE PHILIPS ELECTRONICS N.V., Eindhoven (NL)

(*) Notice: Subject to any disclaimer, the term of this patent is extended or adjusted under 35 U.S.C. 154(b) by 1427 days.

(21) Appl. No.: 13/977,927

(22) PCT Filed: Dec. 22, 2011

(86) PCT No.: PCT/IB2011/055888
§ 371 (c)(1),
(2), (4) Date: Jul. 2, 2013

(87) PCT Pub. No.: WO2012/093311
PCT Pub. Date: Jul. 12, 2012

(65) Prior Publication Data
US 2013/0296716 A1 Nov. 7, 2013

(30) Foreign Application Priority Data
Jan. 6, 2011 (EP) .................................. 11150294

(51) Int. Cl.
*A61B 5/05* (2006.01)
*G06K 7/00* (2006.01)
(Continued)

(52) U.S. Cl.
CPC .......... *G06K 7/0004* (2013.01); *A61B 5/0077* (2013.01); *A61B 5/7495* (2013.01); *G06K 7/10366* (2013.01)

(58) Field of Classification Search
None
See application file for complete search history.

(56) References Cited

U.S. PATENT DOCUMENTS 5,273,036 A * 12/1993 Kronberg ........... A61B 5/02427
600/310
5,573,012 A 11/1996 McEwan
(Continued)

FOREIGN PATENT DOCUMENTS

EP 1623667 A1 2/2006
EP 1653219 A1 5/2006
WO 0173541 A1 10/2001

OTHER PUBLICATIONS

Scalise, L, et al.; Optical Method for Measurement of Respiration Rate; 2010; IEEE Inn Workshop on Medical Measurements and Applications Proceedings; pp. 19-22.
(Continued)

*Primary Examiner* — Jonathan Cwern

(57) ABSTRACT

In order to easily prepare a medical diagnostic analysis of a patient, a barcode scanning device (100) is configured for determining a physiological quantity of the patient. The barcode scanning device (100) comprises a light receiving unit (108) configured for receiving light (219) reflected from a surface to be sensed of the patient, and a signal processing unit (218) configured for determining the physiological quantity of the patient based on the received light (219).

20 Claims, 5 Drawing Sheets

(51) Int. Cl.
*G06K 7/10* (2006.01)
*A61B 5/00* (2006.01)

(56) References Cited

U.S. PATENT DOCUMENTS

| | | | |
|---|---|---|---|
| 2003/0048929 A1* | 3/2003 | Golden et al. | 382/115 |
| 2004/0015091 A1* | 1/2004 | Greenwald | A61B 5/02125 600/513 |
| 2008/0045818 A1* | 2/2008 | Wood | A61B 5/0059 600/310 |
| 2008/0107233 A1* | 5/2008 | Sakaguchi | A61B 6/4233 378/91 |
| 2008/0130015 A1* | 6/2008 | Lu | G01B 11/25 356/610 |
| 2008/0149701 A1 | 6/2008 | Lane | |
| 2008/0228062 A1* | 9/2008 | Zwirn et al. | 600/407 |
| 2009/0048523 A1* | 2/2009 | Schlagheck | A61B 5/0073 600/473 |
| 2010/0046953 A1* | 2/2010 | Shaw et al. | 398/115 |
| 2012/0078088 A1* | 3/2012 | Whitestone | A61B 5/441 600/425 |
| 2013/0060098 A1* | 3/2013 | Thomsen | A61B 5/02028 600/301 |

OTHER PUBLICATIONS

Staderini, E. M.; UWB Radars in Medicine; 2002; IEEE AESS Systems Magazine; pp. 13-18.

\* cited by examiner

BARCODE SCANNING DEVICE FOR DETERMINING A PHYSIOLOGICAL QUANTITY OF A PATIENT

FIELD OF THE INVENTION

The invention relates to a barcode scanning device configured for determining a physiological quantity of a patient.

Further, the invention relates to a method of determining a physiological quantity of a patient.

BACKGROUND OF THE INVENTION

Preparing a medical diagnostic analysis of a patient often comprises a determination of a physiological quantity of the patient. Such quantities may comprise a respiratory frequency or a pulse frequency of the patient which may be associated with a health state of the patient. Determining the physiological quantity of the patient using a contactless technique may allow for non-invasively monitoring the patient, in order to prevent the patient to be exposed to physical loadings.

EP 1 623 667 A1 relates to an apparatus for determining a heart frequency or a respiratory characteristic of a patient using a contactless measuring technique which is based on detecting Doppler induced vibrometric variations of light reflected at an outer surface of the patient. The heart frequency is determined using mathematical procedures relating a motion of the surface to be sensed to a mechanical activity of the heart and of the lungs.

However, such a device for determining a physiological quantity of a patient may be expensive, and may be complicated to operate such that only experienced operators may be able to use the device, in order to prepare a medical diagnostic analysis of the patient.

Further, it is commonly known that a barcode scanning device is usable for reading a one-dimensional or two-dimensional barcode attached to an object, in order to obtain information related to the object and being stored in the one-dimensional or two-dimensional barcode.

US 2008/0149701 A1 describes that that an apparatus configured for generating and displaying a barcode is attachable to a patient. Patient related information, such as a name, an age, a gender, and an address of the patient, as well as medical information of the patient, such as a blood pressure, a temperature, a respiration frequency, and a heart frequency of the patient, may be stored in the displayed barcode. In operation of the apparatus, the displayed barcode is read by a barcode scanner by passing the scanner over the barcode. Accordingly, an operator of the barcode scanner may obtain knowledge about the stored patient information and the stored medical information.

However, preparing a medical diagnostic analysis of a patient using a device for determining a physiological quantity and another device for electronically obtaining further information about the patient may be costly and time-consuming, since multiple devices are necessary for both obtaining information related to the patient and for determining a physiological quantity of the patient.

SUMMARY OF THE INVENTION

It may be an object of the invention to provide an inexpensive, time-saving and easily executable technique for preparing a medical diagnostic analysis of a patient. In particular, it may be an object of the invention to provide a device for and a method of determining a physiological quantity of a patient which may be used during such a preparation of a medical diagnostic analysis of the patient.

In order to achieve the object defined above, a barcode scanning device configured for and a method of determining a physiological quantity of a patient according to the independent claims are provided.

According to an exemplary aspect of the invention, a barcode scanning device configured for determining a physiological quantity of a patient is provided, the barcode scanning device comprising a light receiving unit configured for receiving light reflected from a surface to be sensed of the patient, and a signal processing unit configured for determining the physiological quantity of the patient based on the received light.

According to another exemplary aspect of the invention, a method of determining a physiological quantity of a patient is provided, the method comprising receiving light reflected from a surface to be sensed of the patient by a light receiving unit of a barcode scanning device, and determining the physiological quantity of the patient based on the received light by a signal processing unit of the barcode scanning device.

According to another exemplary aspect of the invention, a use of a barcode scanning device as defined above for preparing a medical diagnostic analysis of a patient is provided.

In the context of this application, the term "physiological quantity" of a patient may particularly denote a measurable value associated with a physiological condition of the patient. For example, the physiological quantity may correspond to a respiratory frequency of the patient being associated with a respiration- or breathing-condition of the patient.

According to the exemplary aspects of the invention, a barcode scanning device may be used for both reading a barcode attached to a patient and for determining a physiological quantity of the patient.

Thus, a preparation of a medical diagnostic analysis of the patient may be executed in an inexpensive, time-saving and easy way, since a single device may be usable for both obtaining information about the patient and for determining a desired physiological quantity of the patient. In particular, a barcode scanning device may represent a conventionally available device having low manufacturing costs. In particular, latency times between obtaining information of the patient and determining the physiological quantity of the patient may be particularly short, since, for example, a mode of the barcode scanning device may only have to be accordingly changed. In particular, operating such a barcode scanning device may be easily executable by professional and non-professional operators of the barcode scanning device, since a barcode scanning device may represent an easy to handle device, thereby facilitating the preparation of the medical diagnostic analysis of the patient. In particular, non-professional operators such as nurses in hospitals or doctor's working assistances in doctor's offices may be enabled to prepare a medical diagnostic analysis of the patient without help of experienced medical staff members.

In particular, a workflow of an operator during a preparation of a medical diagnostic analysis of the patient may be simplified, since the operator may use a single device for executing two steps of the preparation, namely an identification of the patient and a determining of the physiological quantity of the patient, in a natural working sequence.

In particular, an operator of the barcode scanning device may be prevented from being physically fatigued during a preparation of a medical diagnostic analysis of the patient, since a barcode scanning device may represent a compact handheld device, thereby requiring low physical effort of the operator during the determination of the physiological parameter.

Next, further exemplary embodiments of the barcode scanning device configured for determining a physiological quantity of the patient will be explained. However, these embodiments also apply to the respective method and the respective use of the barcode scanning device.

In particular, the received light reflected by the surface to be sensed may comprise ambient light illuminating the surface to be sensed. Accordingly, the barcode scanning device may be free of an additional light emitting unit configured for emitting light towards to the surface to be sensed, thereby facilitating the constructive design of the barcode scanning device.

In particular, the signal processing unit may be configured for reading a barcode attached to the surface to be sensed (particularly of the patient or of an object closely arranged to the patient), whereby information being stored in the read barcode may be obtainable. In particular, such information may comprise patient information of the patient (for example, a name, an age, a gender) or medical information of the patient (for example, information indicating a disease, a medium heart frequency, a medium respiratory frequency of the patient).

The barcode scanning device may further comprise a light emitting unit configured for emitting light towards the surface to be sensed, wherein a wavelength of the emitted light comprises visible light or infrared light. Thus, the visible emitted light emitted by the barcode scanning device may represent an accurate positioning assistance for the operator of the barcode scanning device, in order to precisely focus the light receiving unit towards the surface to be sensed. In particular, since an operator of the barcode scanning device may observe the emitted light spot(s) on the surface to be sensed during the sensing of the surface to be sensed, the operator may be enabled to direct the barcode scanning device towards the surface to be sensed without shaking the barcode scanning device which may potentially hamper or reduce an accurateness of the determination of the physiological quantity of the patient. Accordingly, an alignment of the light receiving unit of the barcode scanning device relative to the surface to be sensed may be improved. In particular, since the emitted light may correspond to visible or infrared light, the barcode scanning device may be usable during poor lighting conditions, for example, during a night, since the emitted light may illuminate a surrounding of the patient and the operator. In particular, the emitted light may be reflected at the surface to be sensed and may be received by the light receiving unit such that the light emitting unit may provide an additional light source for illuminating the surface to be sensed usable during poor lighting conditions.

The emitted light may comprise a light pattern of at least one of a rectangular shape, a rectangularly framed shape, a grid-like shape, and a (particularly single or multiple) spot-like shape. In particular, a combined rectangular and rectangularly framed light pattern may be generated by a light emitting unit emitting light of two different wavelengths (particularly in the visible and/or infrared light ranges) or by the light emitting unit emitting the light of the visible or infrared wavelength and an another light emitting unit emitting light of a different visible or infrared wavelength. In particular, a grid-like shaped light pattern may comprise "lines" of first and second orientations, wherein the first and second orientations may be transverse, particularly perpendicular, to one another. In particular, a spot of the spot-like shaped pattern may comprise a rectangular shape, dotted shape or L-like shape. Thus, since the emitted light may be patterned, aligning the light receiving unit of the barcode scanning device relative to the surface to be sensed may be further facilitated, since the patterned light may provide reference points or marks on the surface to be sensed. In particular, in a case in which the patterned light may comprise several light spots, the operator of the barcode scanning device may be immediately notified when the field of view of the light receiving unit of the barcode scanning device may be rotated or titled owing to movements of the operator of the barcode scanning device. Thus, an accurateness of the determination of the physiological quantity of the patient may be significantly improved.

The light emitting unit may be configured as a laser light emitting unit configured for emitting laser light. In particular, the laser light emitting unit may be configured as a (particularly InGaN based, InGaAs based or AlGaAs based) laser diode or as a (particularly Xenon-Helium based or Xenon based) laser. Thus, the barcode scanning device may comprise a light source of high intensity and of coherent and focused light. Further, a distance between the surface to be sensed (respectively the patient) and the barcode scanning device (respectively the operator) may be significantly enlarged, in order to provide a suitable distance between the patient and the operator during the determination of the physiological quantity of the patient such that the patient may feel comfortable during the preparation of the medical diagnostic analysis.

The light receiving unit may comprise a (particularly Charge-coupled Device (CCD)) camera configured for acquiring an image of the surface to be sensed. Thus, the determining of the physiological quantity of the patient may be significantly fastened particularly in comparison to acquiring single spots of the surface to be sensed, since a two-dimensionally area may simultaneously be sensed.

In particular, the light receiving unit may comprise one or more photodiodes configured for receiving light reflected at portions (for example, points) of the surface to be sensed. In particular, the signal processing unit may comprise an image combining unit configured for combining the acquired portions of the surface to be sensed to an image.

The signal processing unit may comprise an image compensating unit configured for compensating an image acquired based on the received light for (particularly acquiring induced) distortions. In particular, such distortions may be caused by an unevenness of the surface to be sensed, by rotations of the acquired image with respect to a predefined coordination system (particularly defined by a first acquired image) and/or by tilts of the surface to be sensed with respect to a detecting surface of the light receiving unit. Thus, the barcode scanning device may allow for stabilizing an acquired image in terms of compensating for distortions being present on the acquired image and potentially hampering the determination of the physiological quantity of the patient. Accordingly, an accurateness of the determination of the physiological quantity of the patient may be significantly enhanced, since artifacts resulting from the acquiring process of the image may be at least reduced or eliminated.

The image compensating unit may be configured for determining a light pattern (particularly of the emitted light) in the acquired image and for compensating the image based on the determined light pattern. In particular, identifying a light pattern in the acquired image and using the identified light pattern during the compensation procedure may improve the distortion compensation of the acquired image, since features of (the particularly known) light pattern may provide reference points on the surface to be sensed whose relation to one another may be used for correcting distances or angles in the acquired image.

The signal processing unit may comprise a change signal determining unit configured for determining a signal indicative of a change between images (particularly successively) acquired based on the received light, and particularly therefore for operating on the acquired images in a frame-wise way. In particular, the change between the images may comprise a difference of grey or color values between (particularly a point or a portion of) the successively acquired images. In particular, the signal indicative of the change between the images may indicate a changing height or a changing position of (particularly a point or portion of) the surface to be sensed and may represent an image-dependent and thus a time-dependent signal. Accordingly, an evolution of the physiological condition of the patient may be determined using the barcode scanning device, in order to determine the physiological quantity of the patient.

The signal processing unit may comprise a peak determining unit configured for determining a peak of the signal indicative of the change between the images. In this context, the term "peak" may particularly denote a maximum value of the signal or multiple values of the signal. In particular, using a peak (or more peaks) of the signal may allow for an easy and repeatable technique to associate the acquired images with the physiological quantity to be determined.

The peak determining unit may be configured for comparing the signal indicative of the change between the images to a threshold value (which may particularly be a number), wherein a determined peak may comprise a signal portion being at least equal to the threshold value. In particular, the term "signal portion" may particularly denote one signal value or more signal values. Thus, the barcode scanning device may be configured for accurately identifying peaks in the signal and may be particularly configured for differentiating between actual signal values and noise superimposed on the signal. In particular, comparing the signal to a threshold value may be accomplishable by a conventional and easily implementable algorithm, thereby providing an easy technique for determining the peak(s) of the signal.

Additionally or alternatively, the peak determining unit may be configured for determining a maximum (value or maximum values) of the signal indicative of the change between the images particularly by applying a function, for example a Gaussian function or a Lorenzian function, to the signal indicative of the change between the images.

The signal processing unit may comprise a time relating unit configured for relating a number of determined peaks to a receiving time of the light receiving unit associated with the determined peaks. Here, the term "number of determined peaks" may particularly denote a counting number (of each) of the determined peaks or a total number of the determined peaks which may be equal to one or a value greater than one. In particular, the term "receiving time of the light receiving unit associated with the determined peaks" may particularly denote respective receiving time values associated with respective determined peaks or a total receiving time (value) of the light receiving unit. In particular, a receiving time (value) may be obtainable by determining a number of the acquired image(s) and relating this value to the acquiring frequency of the light receiving unit. In particular, a receiving time associated with a determined peak may be selected to correspond to a time value associated with a first signal value of the signal portion being at least equal to the threshold value (when seen along a time evolution of the signal) or a centre value of a receiving time interval associated with the signal portion being at least equal to the threshold value. In particular, the time relating unit may be configured for receiving suitable information about the receiving time, for example the receiving time itself, a number of acquired images as well as an acquiring frequency, or receiving time values associated with respective determined peaks. In particular, the time relating unit may be configured for applying a linear regression of pairs composed of a receiving time value associated with a determined peak and a (counting) number of a determined peak. In particular, a slope of a line of best fit to these pairs may correspond to a value of the physiological quantity. In particular, the time relating unit may be configured for determining a ratio between the (total) number of the determined peaks and the (total) receiving time of the light receiving unit, thereby providing information corresponding to a frequency of an occurrence of an event associated with the physiological condition of the patient associated with the physiological quantity.

At least one of the image compensating unit and the change signal determining unit may be configured for operating on an image acquired based on the received light in a point-wise (or portion-wise) way. In particular, the term "point" may particularly denote a pixel or multiple pixels of an acquired image. Thus, the barcode scanning device may be configured for determining the physiological quantity of the patient simultaneously for multiple image points, thereby improving the accurateness of the determining of the physiological quantity of the patient.

In particular, the peak determining unit may be accordingly configured for operating on multiple signals indicative of the change of the images, wherein each of the signals may be based on a respective portion (for example, point) of the acquired images. In particular, the time relating unit may be accordingly configured for operating on multiple output signals outputted by the peak determining unit, wherein each of the output signals may be based on a respective point of the acquired image.

In particular, the signal processing unit may comprise an averaging unit configured for averaging the multiple output signals outputted by the peak determining unit such that a medium value associated with the physiological quantity of the patient may be obtained. Alternatively, averaging of obtained signals at earlier stages during the determination of the physiological quantity may be executed.

The physiological quantity of the patient may comprise at least one of a respiratory frequency of the patient (particularly measured in number of breaths per minute or second or in Herz) and a pulse frequency of the patient (particularly measured in number of pulse beats per minute or second or in Herz). In particular, the signal indicative of the change between the images may correspond to a change of a height of the surface to be sensed of the patient during a breathing of the patient which may result from a movement of the surface to be sensed during a series of inspiration and expiration acts of the patients. Thus, the barcode scanning device may be usable for determining vital signs of a patient, for example, in a case of an emergency.

In particular, the barcode scanning device may be configured for simultaneously or subsequently reading a barcode attached to the surface to be sensed and for determining a physiological quantity of the patient. In particular, a sequence of both operations may be interchangeable.

In particular, the barcode scanning device may be configured for acquiring images of the surface to be sensed and timely spaced determining the physiological quantity of the patient.

In particular, the barcode scanning device may comprise a storage unit configured for storing information associated with the determination of the physiological quantity of the patient and/or reading the barcode.

In particular, (respective units of) the signal processing unit may be embodied in one or more processors comprising integrated circuits with suitable electronic components such as power supply units, diodes, transistors, integrators, and/or logical components such as AND-, OR-, or NOR-gates.

BRIEF DESCRIPTION OF THE DRAWINGS

The invention will be described in more detail hereinafter with reference to examples of embodiment, but to which the invention is not limited.

DETAILED DESCRIPTION OF EMBODIMENTS

Figure 1:
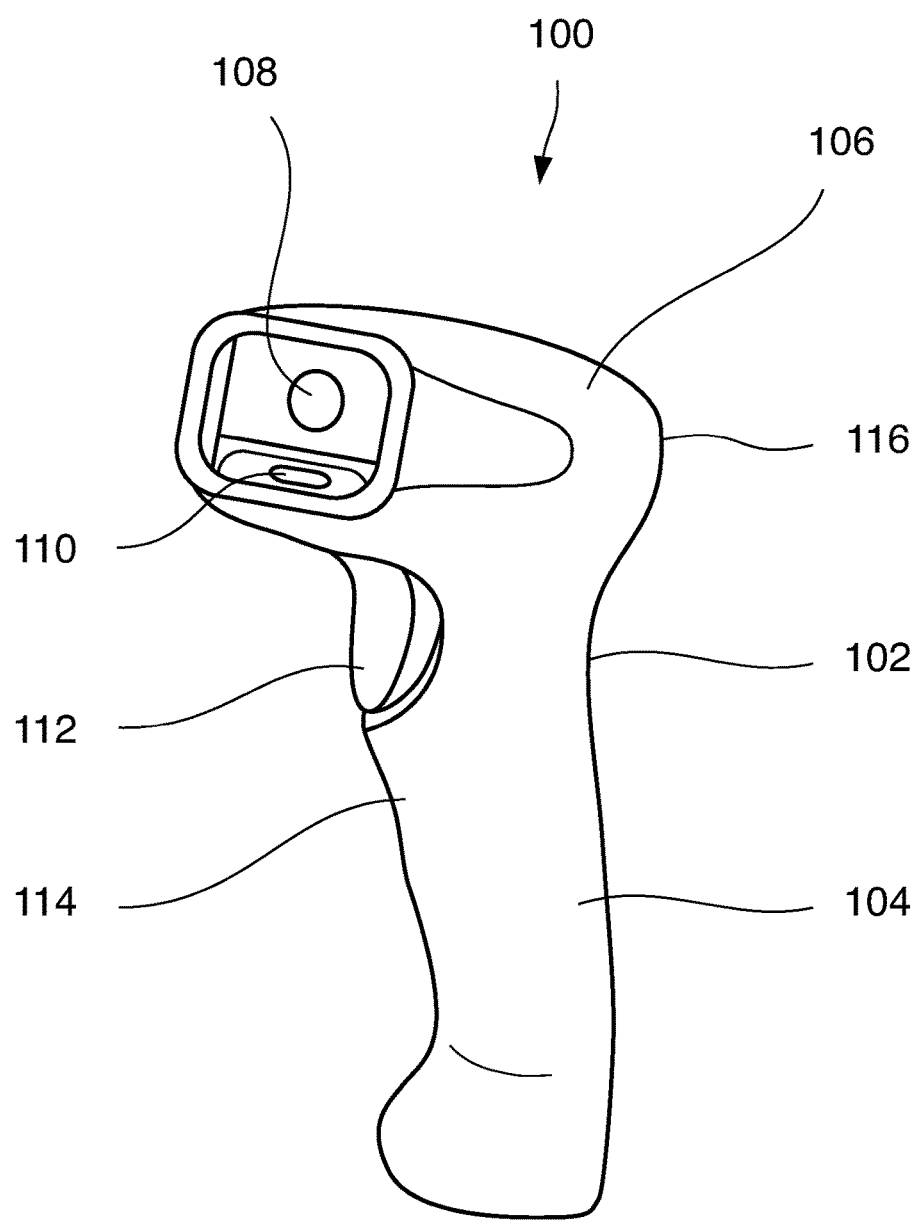
FIG. 1 illustrates a perspective view of a barcode scanning device for determining a respiratory frequency of a patient according to an exemplary embodiment of the invention.

The illustration in the drawing is schematic. It is noted that in different figures, similar or identical elements are provided with the same reference signs or with reference signs which are different from the corresponding reference signs only with the first digit.

Referring to FIG. 1, a barcode scanning device 100 according to an exemplary embodiment of the invention is illustrated. The barcode scanning device 100 is configured for determining a respiratory frequency of a patient, in order to prepare a medical diagnostic analysis of the patient.

To this end, the barcode scanning device 100 is configured as a handheld device comprising a housing 102 having first and second housing portions 104, 106. The first housing portion 104 is shaped as a handgrip such that an operator of the barcode scanning device 100 may comfortably hold the barcode scanning device 100 with his hand. The second housing portion 106 is configured as an elongated flat portion and accommodates a Charge-coupled Device (CCD) camera 108, a light emitting unit 110 in the form of an InGaAs based laser diode, and a signal processing unit.

The CCD camera 108 is configured for acquiring framewise images at an acquiring frequency of 1.5 images (or frames) per second. An image size of the acquired images corresponds to 36 millimeter times 24 millimeter, and a pixel size of an acquired image corresponds to 1.5 micrometer times 1.5 micrometer.

The laser diode light emitting unit 110 is configured for emitting laser light of a wavelength of 1.0 μm, thereby emitting infrared laser light. Further, the emitted laser light comprises a rectangularly framed light pattern having a grid defined by vertically and horizontally arranged lines. The light pattern of the emitted laser light is dimensioned to be smaller in size compared to a field of view of the CCD camera 108.

Further, the barcode scanning device 100 comprises two actuators 112 each of which being configured as a knob. The first actuator 112 is arranged at a front side 114 of the first housing portion 104 adjacent to the second housing portion 106. The first actuator 112 is pushable for activating the laser diode light emitting unit 110 such that the patterned laser light is emitted. The second actuator is arranged at a rear side 116 of the second housing portion 106 and is pushable for activating the CCD camera 108 to acquire images.

Figure 2:
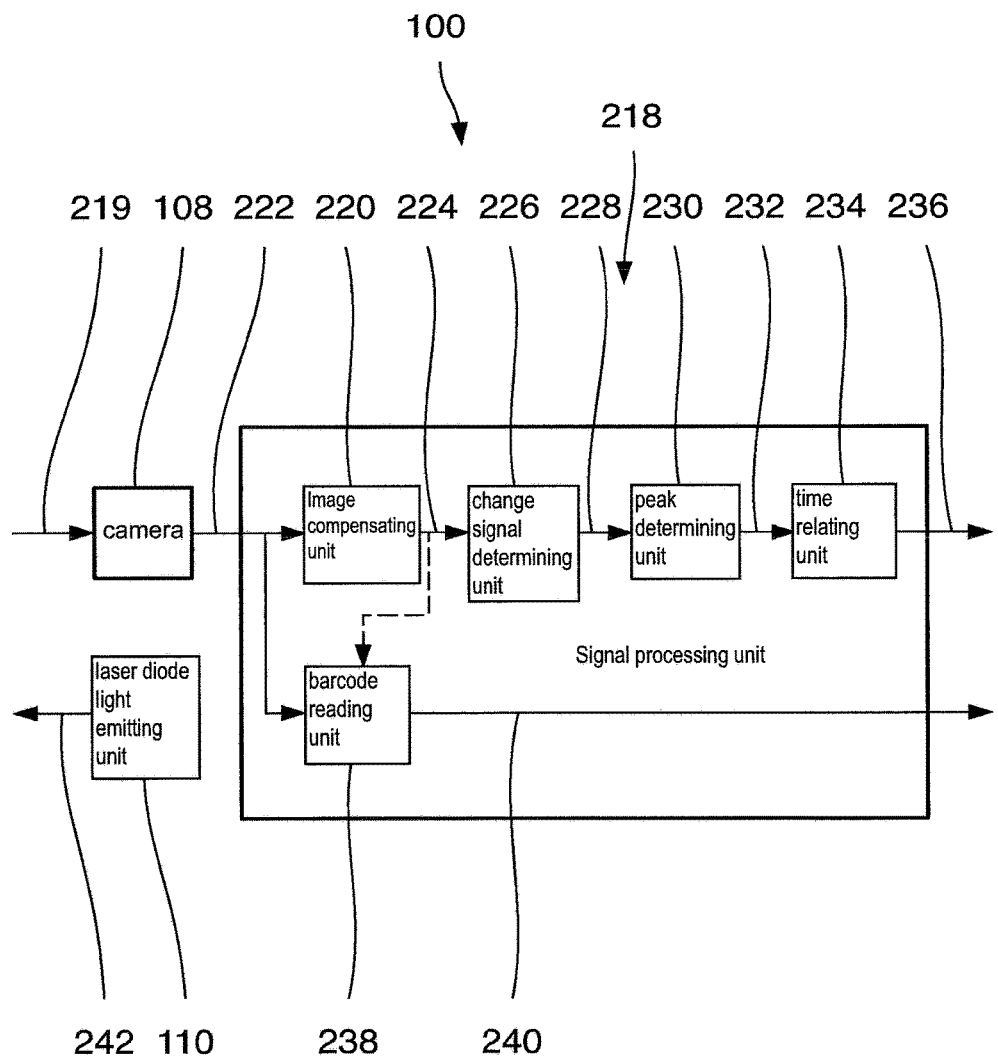
FIG. 2 is a block diagram illustrating the barcode scanning device of FIG. 1.

Referring to FIG. 2, the signal processing unit of the barcode scanning device 100 is illustrated in more detail.

The signal processing unit now denoted by a reference numeral 218 is configured for determining the respiratory frequency of the patient based on light 219 received by the CCD camera 108 and for reading a barcode attached to the patient based on the received light 219.

Figure 4:
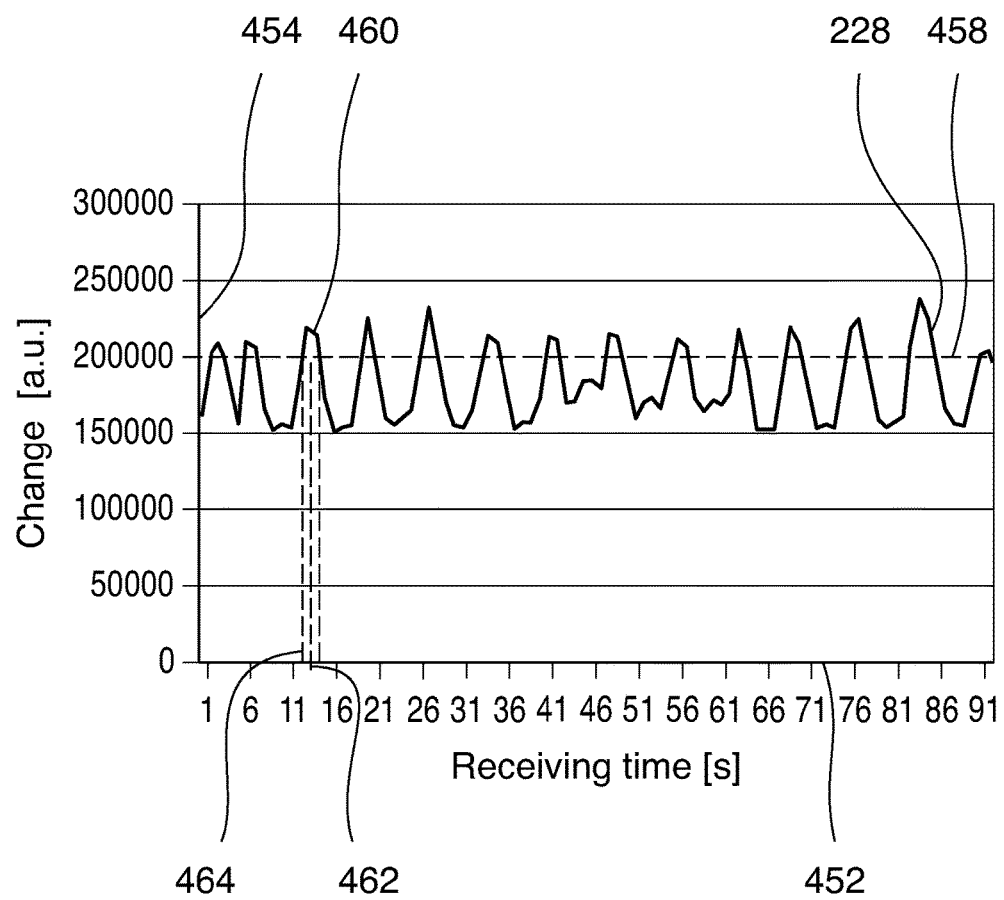
FIG. 4 is a diagram illustrating a receiving time dependency of a signal indicative of a change between images successively acquired using the barcode scanning device of FIG. 1.

In order to determine the respiratory frequency of the patient, the signal processing unit 218 comprises an image compensating unit 220 configured for compensating an image 222 which is acquired and outputted by the CCD camera 108 based on the received light 219 for distortions. Image processing techniques applied to the acquired images 222 may include rotating, tilting, flatting, and/or rectifying the images 222. The image compensating unit 220 is configured for outputting a compensated image 224. Further, the signal processing unit 218 comprises a change signal determining unit 226 configured for operating on the outputted compensated images 224 and for determining a signal 228 indicative of a change between successively acquired images 222. The output signal 228 of the change signal determining unit 226 corresponds to a receiving time dependency of the change between the successively acquired images 222, an example of which is illustrated in FIG. 4 in more detail. Further, the signal processing unit 218 comprises a peak determining unit 230 configured for operating on the output signal 228 of the change signal determining unit 226 and for determining peaks of the signal 228 indicative of the change between the acquired images 222. An output signal 232 of the peak determining unit 230 comprises the form of a table with a first entry of the table corresponding to the receiving time value associated with a respective determined peak of the signal 228 and a second entry of the table corresponding to a counting number of the determined peak. A time relating unit 234 of the signal processing unit 218 is configured for operating on the output signal 232 of the peak determining unit 230 and for relating a number of the determined peaks to the receiving time associated with the determined peaks. In particular, the time relating unit 234 is configured for applying a linear regression to the received pairs of the table composed of the first and second entries. An output signal 236 of the time relating unit 234 comprises the respiratory frequency of the patient.

Instead of outputting the receiving time dependent signal 228 the change signal determining unit 226 is configured for outputting an image counting number dependant signal indicative of the change between the successively acquired images 222, i.e. the signal 228 has an implicit receiving time dependency. Accordingly, the peak determining unit 230 is configured for determining the peaks relative to a counting number of the acquired images 222. An output signal of the peak determining unit 230 corresponds to a table having first entries identical to the counting numbers of an acquired image associated with a determined peak and second entries identical to the counting numbers of the determined peak. Accordingly, the time relating unit 234 is configured for associating the numbers of the acquired images to receiving time values associated with the determined peak using the known acquiring frequency of the CCD camera 108 and for applying a linear regression as described above.

Alternatively, the time relating unit 234 is configured for calculating a ratio between the total number of the determined peaks and a total receiving time of the CCD camera 108.

Further, in order to read a barcode attached to the patient, the signal processing unit 218 comprises a barcode reading unit 238 configured for operating on one of the acquired images 222 and for reading the barcode being displayed in the one acquired image 222. An output signal 240 of the barcode reading unit 136 corresponds to information stored in the read barcode. Alternatively, as indicated by a dashed line in FIG. 2, the barcode reading unit 238 is configured for operating on the compensated image 224 outputted by the image compensating unit 220.

A light emitted by the laser diode light emitting unit 110 is denoted by a reference numeral 242.

Further, the barcode scanning device 100 is wirelessly coupled to a display device configured for displaying the determined respiratory rate and the read information stored in the barcode.

In operation of the barcode scanning device 100, an operator of the barcode scanning device 100 directs the CCD camera 108 and the laser diode light emitting unit 110 to a barcode 341 attached to an arm 342 of a patient 344. The operator pushes the actuator arranged at the rear side 116 of the barcode scanning device 100 such that images 222 are continuously acquired. Ambient light illuminates the barcode 341. The light 219 reflected by the barcode 341 is received by the CCD camera 108 which accordingly outputs successive images 222, which are, in turn, supplied to the barcode reading unit 238 of the signal processing unit 218. Accordingly, the barcode reading unit 238 uses one of the acquired images 222 for reading the barcode 341 and outputs the signal 240 comprising the information stored in the barcode 341. This information comprises a name, an age, and a gender of the patient 344. The information is transferred to the display device.

Next, the operator of the barcode scanning device 100 directs the camera 108 to an abdominal section 346 of the patient, in order to determine the respiratory frequency of the patient 344. The operator pushes the actuator 112 attached to the front side 114 of the barcode scanning device 100 and also the actuator attached to the rear side 116 of the barcode scanning device 100 such that both the laser diode light emitting unit 110 and the CCD camera 108 are activated. Accordingly, the laser diode light emitting unit 110 outputs the laser light 242 having the above described pattern now denoted by a reference numeral 348. The laser light 242 is incident on a surface 350 to be sensed of the abdominal section 346 of the patient 344 which corresponds to a field of view of the CCD camera 108 defining dimensions of the acquired images 222. The surface 350 to be sensed is dimensioned to be greater than an area on which the light pattern 348 is incident.

The CCD camera 108 receives the light 219 reflected by the surface 350 to be sensed such that the CCD camera 108 outputs images 222 displaying the surface 350 to be sensed including the light pattern 348. The acquired images 222 are received by the image compensating unit 220 which stabilizes the acquired images 222 in that the acquired images 222 are rotated and tilted relative to one another such that the surface 350 to be sensed depicted in the acquired images 222 coincide in all images 222. Further, as the surface 350 to be sensed is unevenly shaped owing to the moving and curved surface of the abdominal section 346 of the patient 344 during breathing, the image compensating unit 330 distorts the acquired images 222 such that the outputted images 224 depict a virtually "even" surface 350 to be sensed. To this end, the image compensating unit 220 identifies the acquired light pattern 348 in the acquired images 222 and rectifies the acquired light pattern 348 to obtain the compensated image 224 comprising the original shape of the light pattern emitted by the laser diode light emitting unit 110. The change signal determining unit 226 receives the compensated images 224 and outputs the signal 228 indicative of the change of a height of the surface 350 to be sensed of the patient 344 between successively acquired images 222.

Referring to FIG. 4, the receiving time dependency of the signal 228 is illustrated. An abscissa 452 of the diagram corresponds to the receiving time measured in units of seconds, and an ordinate 454 of the diagram corresponds to the change of the height measured in arbitrary units. Although having discrete values, the signal 228 is illustrated by a continuous line in FIG. 4. The signal 228 comprises a periodically raising and falling shape which is caused by inspiration and expiration acts of the patient 344 during a breathing.

The peak determining unit 230 receives the signal 228 and determines respective peaks of the signal 228 by applying a threshold value 458, namely the number 200000, to the signal 228 and by identifying those signal portions of the signal 228 which are at least equal to the threshold value 458. In the shown embodiment, the peak determining unit 230 identifies fourteen peaks 160 of the signal 228. The peak determining unit 230 also determines a receiving time value 462 for each of the determined peaks 460 corresponding to a centre value of a respective receiving time interval 464 which is associated with the determined peak 460. For illustration purposes, only the third peak 460 and the respective centre receiving time value 462 is indicated by reference numerals. The peak determining unit 230 outputs the table having the first entries corresponding to the receiving time values of each of the determined peaks 460 and the second entries corresponding to counting numbers of the determined peaks 460. The time relating unit 234 receives the table 232 outputted by the peak determining unit 230 and applies a linear regression to the received table pairs composed of the first and second entries, in order to determine the respiratory frequency 236 of the patient 344. Here, the respiratory frequency corresponds to a slope of a line of best fit to the table pairs. In the shown embodiment, the determined respiratory frequency 236 corresponds to 0.15 respirations per second or 9.2 respirations per minute.

Alternatively, as explained above with reference to FIG. 2, the peak determining unit 230 counts the number of peaks of the signal 228 using the threshold value 458 and outputs the total number of determined peaks 460 and the total receiving time of the CCD camera 108. The time relating unit 234 then calculates the respiratory frequency by dividing the total number of determined peaks 460 by the total receiving time.

The outputted signal indicating the respiratory frequency is transferred to the display device such that the operator of the barcode scanning device 100 may use this information for preparing the medical diagnostic analysis of the patient 344.

Figure 5:
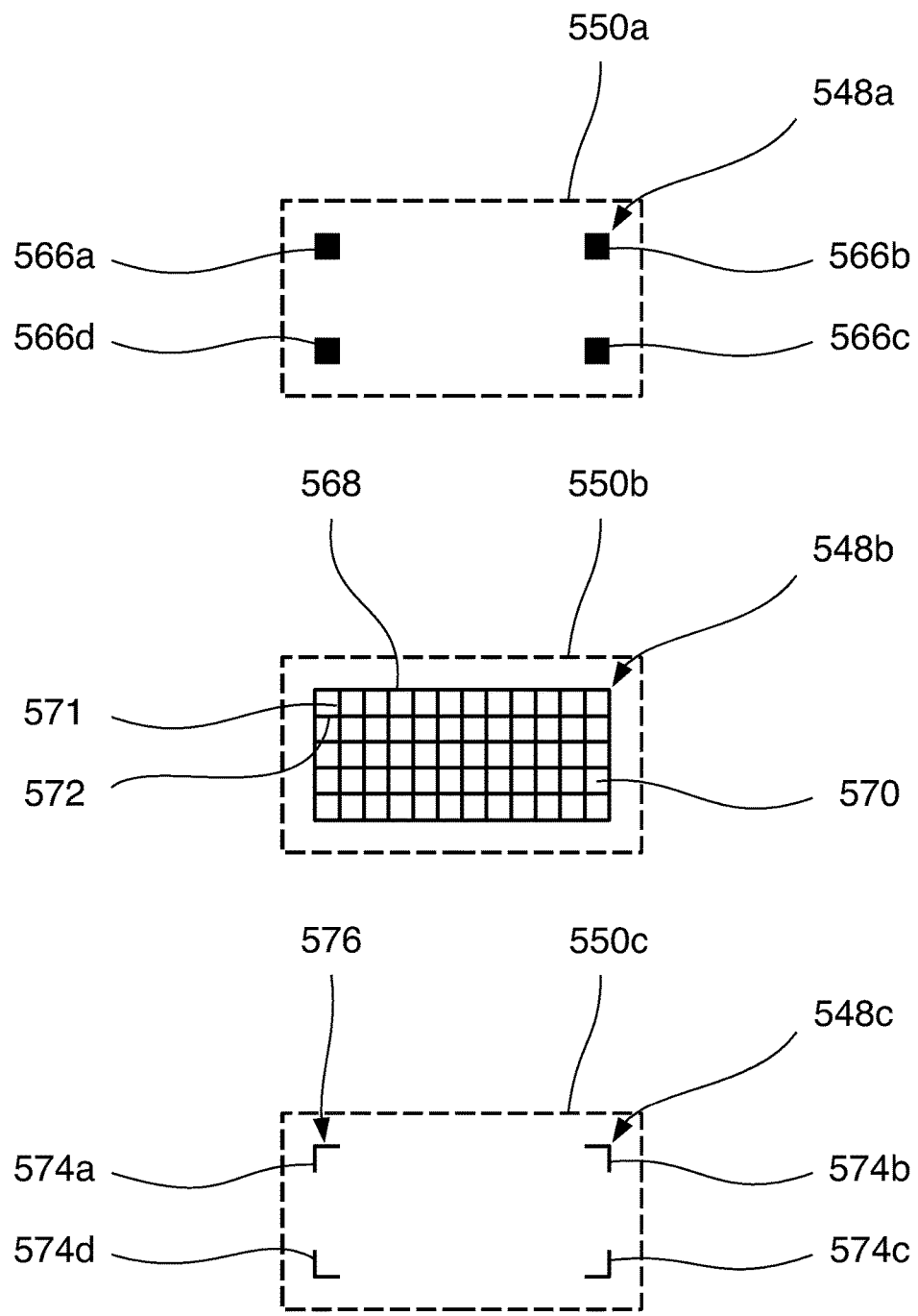
FIG. 5 illustrates exemplary embodiments of a light pattern of light emitted by a light emitting unit of the barcode scanning device in FIG. 1.

Referring to FIG. 5, embodiments of a light pattern 548 of the emitted light 242 are illustrated. For comparison, the surface 550 to be sensed is also illustrated.

A light pattern 548a illustrated in an upper portion of FIG. 5 is rectangular shaped and comprises four rectangular shaped spots 564a-d defining outer edges of the rectangular frame of the light pattern 548a.

Figure 3:
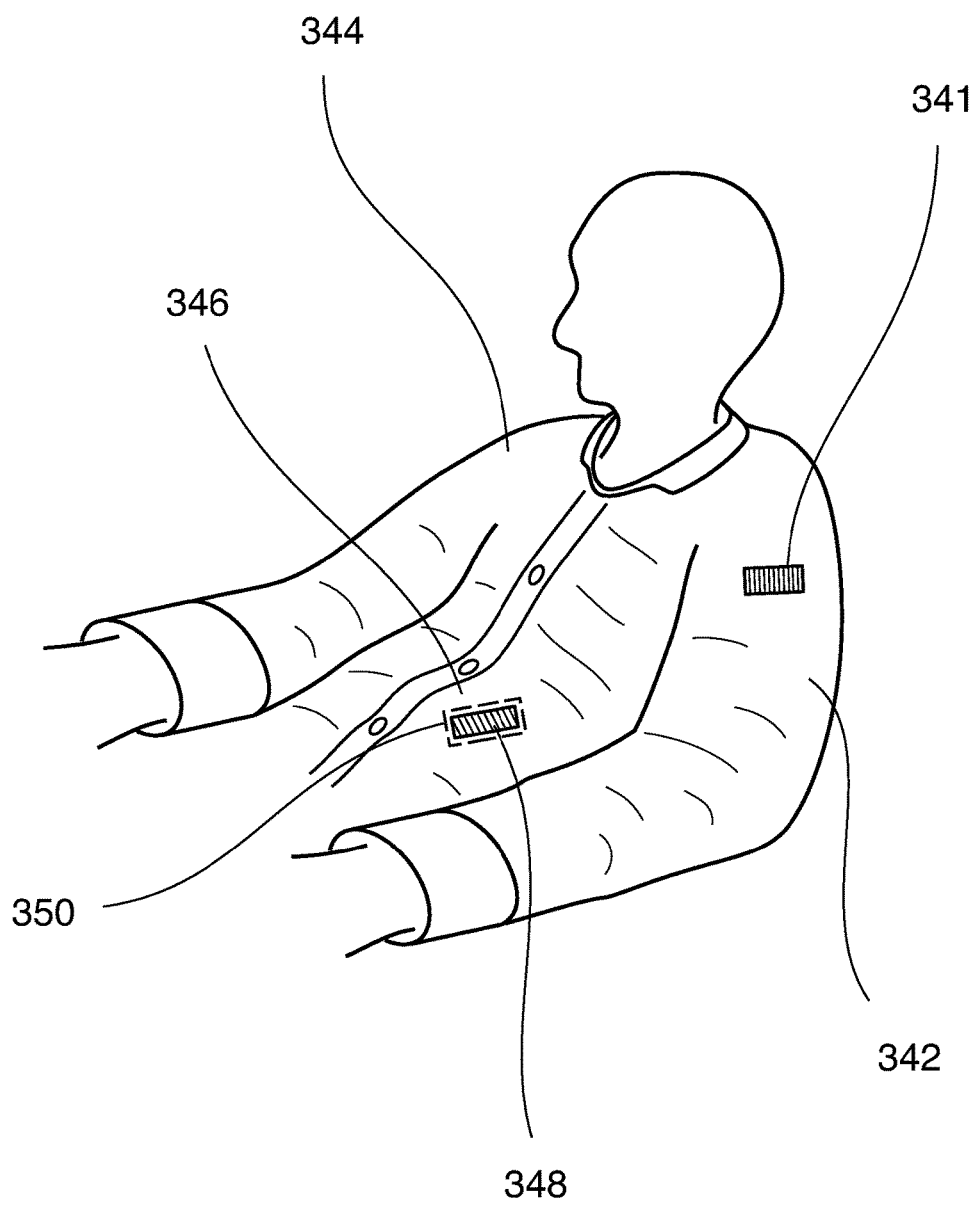
FIG. 3 illustrates a perspective view of a patient during a determination of a respiratory frequency of the patient using the barcode scanning device of FIG. 1.

As illustrated in a middle portion of FIG. 5, a light pattern 548b is rectangular shaped and comprises a rectangular frame 568 and a grid 570 composed of vertical lines 571 and horizontal lines 572. This light pattern 548b corresponds to the light pattern 348 depicted in FIG. 3 and being distorted owing to the curved surface 350 to be sensed.

As illustrated in a lower portion of FIG. 5, a light pattern 548c is rectangular shaped and comprises L-shaped spots 574a-d defining corner edges of a rectangular frame 576 of the light pattern 548c.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A barcode scanning device configured both for reading a barcode attached to a patient and for determining a physiological quantity of the patient wherein the physiological quantity of the patient comprises at least one of a respiratory frequency of the patient or a pulse frequency of the patient, the barcode scanning device comprising:
   a light emitting unit configured for emitting light towards a surface to be sensed of the patient, wherein a wavelength of the emitted light comprises visible light or infrared light, and wherein the emitted light comprises a light pattern of at least one of a rectangular shape, a rectangular framed shape, a grid shape, and a spot shape,
   a light receiving unit configured for:
      (i) receiving light reflected from a surface to be sensed of the patient, and
      (ii) acquiring images based on the received light, and
   a signal processing unit configured for: (i) reading a barcode, and (ii) determining the physiological quantity of the patient based on the received light, wherein the signal processing unit comprises:
      (i) a change signal determining unit configured for determining a signal indicative of a change between the images acquired based on the received light, and
      (ii) a peak detector configured for determining a peak of the signal indicative of the change between the acquired images.

2. The barcode scanning device according to claim 1, wherein the light emitting unit comprises a laser configured for emitting laser light.

3. The barcode scanning device according to claim 1, wherein the light receiving unit comprises a camera configured for acquiring an image of the surface to be sensed.

4. The barcode scanning device according to claim 1, wherein the signal processing unit comprises an image compensating unit configured for compensating an image acquired based on the received light for distortions.

5. The barcode scanning device according to claim 4, wherein the image compensating unit is configured for determining a light pattern in the acquired image and for compensating the image based on the determined light pattern.

6. The barcode scanning device according to claim 5, wherein the light pattern provides reference points, and the image compensating unit is further configured for using the reference points to correct an angle in an acquired image.

7. The barcode scanning device according to claim 4, wherein the image compensating unit is further configured for producing a plurality of compensated images; and
   wherein the barcode scanning device further comprises a barcode reading unit configured for reading a barcode from a compensated image of the plurality of compensated images produced by the image compensating unit.

8. The barcode scanning device according to claim 7, wherein the signal processing unit is further configured for determining the respiratory frequency from the plurality of compensated images.

9. The barcode scanning device according to claim 1, wherein the peak detector is configured for comparing the signal indicative of the change between the images to a threshold value, wherein a determined peak comprises a signal portion being at least equal to the threshold value.

10. The barcode scanning device according to claim 1, wherein the signal processing unit comprises a time relating unit configured for relating a number of determined peaks to a receiving time of the light receiving unit associated with the determined peaks.

11. The barcode scanning device according to claim 1, wherein the peak detector is further configured to perform operations in a point-wise way by operating on multiple signals indicative of the change between the images, wherein each of the multiple signals is based on a respective point of the acquired images.

12. The barcode scanning device according to claim 1, wherein the signal processing unit is configured to determine at least one of the respiratory frequency or the pulse frequency of the patient based on the received light.

13. A method of determining at least one of a respiratory frequency of a patient or a pulse frequency of the patient with a single device, the method comprising:
   emitting light towards a surface of the patent to be sensed, wherein the emitted light comprises a light pattern of at least one of a rectangular shape, a rectangular framed shape, a grid shape, and a spot shape,
   receiving light reflected from the surface of the patent to be sensed by a light receiving unit of a barcode scanning device,
   acquiring images based on the received light,
   determining at least one of the respiratory frequency or the pulse frequency of the patient based on the received light by a signal processing unit of the barcode scanning device,
   determining a signal indicative of a change between images acquired based on the received light, and
   determining a peak of the signal indicative of the change between the images.

14. A scanning device configured to both read a barcode attached to a patient and to determine at least one of a respiratory frequency and a pulse frequency of the patient, the scanning device comprising:
- a laser configured to emit a pattern of visible or infrared light toward the attached barcode and towards a surface of the patient to be sensed;
- a camera configured to:
  - (i) receive light reflected from the barcode and from the surface of the patient to be sensed; and
  - (ii) acquire images based on the received light; and
- a signal processor configured to:
  - (i) determine an identification of the patient based on the light reflected from the barcode;
  - (ii) determine at least one of the respiratory frequency and the pulse frequency of the patient based on the light reflected from the surface of the patient; and
  - (iii) determine a peak of a signal indicative of a change between the acquired images.

15. The scanning device according to claim 14, wherein the signal processor is further configured to determine a change between images acquired based on the reflected light.

16. The scanning device according to claim 14, wherein the signal processor is further configured to determine distortions in an image based on the received reflected light reflected from the surface, determine a light pattern in the acquired image, and compensate the acquired image based on the determined light pattern.

17. The scanning device according to claim 14, wherein the signal processor is further configured to determine changes in the reflected light from the surface of the patient received by the camera and compare the change to a threshold value.

18. The scanning device according to claim 17, wherein the signal processor is further configured to associate a time when the reflected light from the surface exceeds the threshold value, the signal processor configured to generate an output that includes the identification of the patient, and at least one of the respiratory frequency and the pulse frequency, and the associated time.

19. The scanning device according to claim 14, wherein the signal processor is further configured to:
- determine the respiratory frequency from the acquired images; and
- read the barcode from at least one of the acquired images.

20. The scanning device according to claim 14, wherein the signal processor is further configured to determine the pulse frequency of the patient.

* * * * *